(12) United States Patent
Kusters et al.

(10) Patent No.: US 11,325,321 B2
(45) Date of Patent: May 10, 2022

(54) APPARATUS AND METHOD FOR MECHANICALLY OPENING A CONNECTION SITE

(71) Applicant: Fenwal, Inc., Lake Zurich, IL (US)

(72) Inventors: Benjamin E. Kusters, Pleasant Prairie, WI (US); Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 17/147,660

(22) Filed: Jan. 13, 2021

(65) Prior Publication Data

US 2021/0138739 A1 May 13, 2021

Related U.S. Application Data

(62) Division of application No. 15/978,487, filed on May 14, 2018, now Pat. No. 10,919,235.

(Continued)

(51) Int. Cl.
*A61M 39/14* (2006.01)
*B29C 65/00* (2006.01)
*A61M 39/18* (2006.01)
*B29C 57/10* (2006.01)
*B29C 65/74* (2006.01)

(Continued)

(52) U.S. Cl.
CPC ......... *B29C 66/0324* (2013.01); *A61M 39/14* (2013.01); *A61M 39/143* (2013.01); *A61M 39/146* (2013.01); *A61M 39/18* (2013.01); *B29C 57/10* (2013.01); *B29C 65/7455* (2013.01); *B29C 66/1142* (2013.01); *B29C 66/5221* (2013.01); *B29C 66/73921* (2013.01); *B29C 66/857* (2013.01); *B29C 65/02* (2013.01); *B29C 66/71* (2013.01); *B29K 2027/06* (2013.01); *B29L 2023/007* (2013.01)

(58) Field of Classification Search
CPC ............. B29C 66/1142; B29C 66/5221; B29C 66/0321; A61M 39/143
See application file for complete search history.

(56) References Cited

U.S. PATENT DOCUMENTS 4,157,723 A  6/1979  Granzow et al.
4,369,779 A  1/1983  Spencer
(Continued)

FOREIGN PATENT DOCUMENTS

EP  0104737 A1  4/1984
EP  0107270 A1  5/1984
(Continued)

OTHER PUBLICATIONS

European Patent Office, Extended European Search Report, counterpart EP Appl No. 18173887, dated Oct. 19, 2018 (7 pages).

*Primary Examiner* — Scott W Dodds
(74) *Attorney, Agent, or Firm* — Cook Alex Ltd.

(57) ABSTRACT

Method and apparatus are disclosed for mechanically opening a heat-bonded connection site between two hollow, flexible, thermoplastic segments of a medical fluid flow path, the heat-bonded connection site having an axis. The connection site is compressed between two facing surfaces, and the facing surfaces are relatively moved to rotate the connection site about the connection site axis and to apply force to the connection site substantially perpendicular to the connection site axis.

20 Claims, 12 Drawing Sheets

Related U.S. Application Data

(60) Provisional application No. 62/516,214, filed on Jun. 7, 2017.

(51) Int. Cl.
- B29C 65/02 (2006.01)
- B29K 27/06 (2006.01)
- B29L 23/00 (2006.01)

(56) References Cited

U.S. PATENT DOCUMENTS

| | | |
|---|---|---|
| 4,412,835 A | 11/1983 | Spencer |
| 4,476,631 A | 10/1984 | Benin |
| 4,501,951 A | 2/1985 | Benin et al. |
| 4,507,119 A | 3/1985 | Spencer |
| 4,516,971 A | 5/1985 | Spencer |
| 4,521,263 A | 6/1985 | Benin et al. |
| 4,610,670 A | 9/1986 | Spencer |
| 4,619,642 A | 10/1986 | Spencer |
| 4,633,063 A | 12/1986 | Willis |
| 4,647,756 A | 3/1987 | Willis |
| 4,737,214 A | 4/1988 | Leurink et al. |
| 4,753,697 A | 6/1988 | Shaposka et al. |
| 4,770,735 A | 9/1988 | Shaposka et al. |
| 4,793,880 A | 12/1988 | Shaposka et al. |
| 4,832,773 A | 5/1989 | Shaposka et al. |
| 4,897,138 A | 1/1990 | Shaposka et al. |
| 4,913,756 A | 4/1990 | Shaposka et al. |
| 4,933,036 A | 6/1990 | Shaposka et al. |
| 5,009,645 A | 4/1991 | Silver et al. |
| 5,141,592 A | 8/1992 | Shaposka et al. |
| 5,156,701 A | 10/1992 | Spencer et al. |
| 5,158,630 A | 10/1992 | Shaposka et al. |
| 5,209,800 A | 5/1993 | Spencer et al. |
| 5,221,267 A | 6/1993 | Folden |
| 5,244,522 A | 9/1993 | Spencer et al. |
| 5,248,359 A | 9/1993 | Shaposka et al. |
| 5,250,041 A | 10/1993 | Folden et al. |
| 5,256,229 A | 10/1993 | Spencer |
| 5,270,003 A | 12/1993 | Bernes et al. |
| 5,279,685 A | 1/1994 | Ivansons et al. |
| 5,397,425 A | 3/1995 | Ivansons et al. |
| 5,518,575 A | 5/1996 | Watanabe |
| 5,554,253 A | 9/1996 | Watanabe |
| 5,632,852 A | 5/1997 | Ivansons et al. |
| 5,674,333 A | 10/1997 | Spencer |
| 5,674,741 A * | 10/1997 | Watanabe ............. B29C 66/818 435/283.1 |
| 5,802,689 A | 9/1998 | Sano |
| 5,836,619 A | 11/1998 | Shemesh et al. |
| 5,855,731 A | 1/1999 | Spencer |
| 6,177,652 B1 | 1/2001 | Ivansons |
| 6,322,551 B1 | 11/2001 | Brugger |
| 6,460,592 B1 | 10/2002 | Sano et al. |
| 6,463,979 B1 | 10/2002 | Sano et al. |
| 6,485,593 B1 | 11/2002 | Christoffersen |
| 6,705,372 B2 | 3/2004 | Sano et al. |
| 6,913,056 B2 | 7/2005 | Landherr et al. |
| 7,070,589 B2 | 7/2006 | Lolachi et al. |
| 7,119,305 B2 | 10/2006 | Sano et al. |
| 7,122,094 B2 | 10/2006 | Baradon et al. |
| 7,371,305 B2 | 5/2008 | Sano et al. |
| 7,398,813 B2 | 7/2008 | Ivansons et al. |
| 7,459,054 B2 | 12/2008 | Landherr et al. |
| 7,657,996 B2 | 2/2010 | Sano et al. |
| 7,766,394 B2 | 8/2010 | Sage et al. |
| 7,779,880 B2 | 8/2010 | Sano et al. |
| 7,922,848 B2 | 4/2011 | Ishida et al. |
| 7,964,048 B2 | 6/2011 | Hlavinka et al. |
| 8,146,642 B2 | 4/2012 | Landherr et al. |
| 8,708,019 B2 | 4/2014 | Ivansons et al. |
| 8,857,485 B2 | 10/2014 | Bühler et al. |
| 9,199,070 B2 | 12/2015 | Wegener et al. |
| 9,205,612 B2 | 12/2015 | Ivansons et al. |
| 9,533,135 B2 | 1/2017 | Kusters et al. |
| 2013/0153048 A1 | 6/2013 | Schwalm et al. |
| 2014/0077488 A1 | 3/2014 | Wegener et al. |
| 2015/0367120 A1 | 12/2015 | Kusters et al. |
| 2016/0082245 A1 | 3/2016 | Gebauer et al. |
| 2016/0082651 A1 | 3/2016 | Ivansons et al. |
| 2016/0250806 A1 | 9/2016 | Chengalvarayan et al. |
| 2016/0361531 A1 | 12/2016 | Kusters et al. |

FOREIGN PATENT DOCUMENTS

| | | |
|---|---|---|
| EP | 0044204 B1 | 4/1985 |
| EP | 0139350 A1 | 5/1985 |
| EP | 0103977 B1 | 11/1986 |
| EP | 0104718 B1 | 11/1986 |
| EP | 0105587 B1 | 8/1987 |
| EP | 0208004 B1 | 8/1988 |
| EP | 0134630 B1 | 5/1989 |
| EP | 0194873 B1 | 7/1991 |
| EP | 0619175 A2 | 10/1994 |
| EP | 0507321 B1 | 6/1995 |
| EP | 0723851 A2 | 7/1996 |
| EP | 0728274 A1 | 8/1996 |
| EP | 0471953 B1 | 9/1999 |
| EP | 0599057 B1 | 12/1999 |
| EP | 0515811 B1 | 8/2000 |
| EP | 0623032 B1 | 8/2001 |
| EP | 0483478 B1 | 11/2001 |
| EP | 0508373 B1 | 12/2001 |
| EP | 0583582 B1 | 1/2002 |
| EP | 0778123 B1 | 4/2002 |
| EP | 0649727 B1 | 5/2002 |
| EP | 0903214 B1 | 5/2002 |
| EP | 1238782 A1 | 9/2002 |
| EP | 1244542 B1 | 6/2003 |
| EP | 1048316 B1 | 10/2003 |
| EP | 1066853 B1 | 9/2004 |
| EP | 0731540 B1 | 10/2004 |
| EP | 1048315 B1 | 6/2005 |
| EP | 2089094 B1 | 1/2007 |
| EP | 1438981 B1 | 2/2009 |
| EP | 1346749 B1 | 3/2009 |
| EP | 1579983 B1 | 4/2009 |
| EP | 1438982 B1 | 3/2011 |
| EP | 2301620 A1 | 3/2011 |
| EP | 1640142 B1 | 4/2011 |
| EP | 1652653 B1 | 6/2011 |
| EP | 1867359 B1 | 2/2012 |
| EP | 2420286 A1 | 2/2012 |
| EP | 2419257 B1 | 3/2013 |
| EP | 1108444 B1 | 4/2014 |
| EP | 2046560 B1 | 5/2014 |
| EP | 2774747 A1 | 9/2014 |
| EP | 1555111 B1 | 1/2015 |
| EP | 2957402 A1 | 12/2015 |
| EP | 1547755 B1 | 2/2016 |
| EP | 2999513 A1 | 3/2016 |
| WO | WO92/05945 A2 | 4/1992 |
| WO | WO94/12224 A1 | 6/1994 |
| WO | WO01/47692 A1 | 7/2001 |
| WO | WO02/066098 A1 | 8/2002 |
| WO | WO03/063940 A2 | 8/2003 |
| WO | WO2004/020179 A1 | 3/2004 |
| WO | WO2004/022317 A1 | 3/2004 |
| WO | WO2004/039563 A1 | 5/2004 |
| WO | WO2005/000564 A1 | 1/2005 |
| WO | WO2005/000565 A1 | 1/2005 |
| WO | WO2008/016777 A2 | 2/2008 |
| WO | WO2008/054699 A2 | 5/2008 |
| WO | WO2010/118546 A1 | 10/2010 |
| WO | WO2011/144561 A1 | 11/2011 |
| WO | WO2012/022635 A2 | 2/2012 |
| WO | WO2013/004322 A1 | 1/2013 |
| WO | WO2013/096038 A1 | 6/2013 |
| WO | WO2014/189446 A1 | 11/2014 |
| WO | WO2015/060774 A1 | 4/2015 |
| WO | WO2017/093216 A1 | 6/2017 |

\* cited by examiner

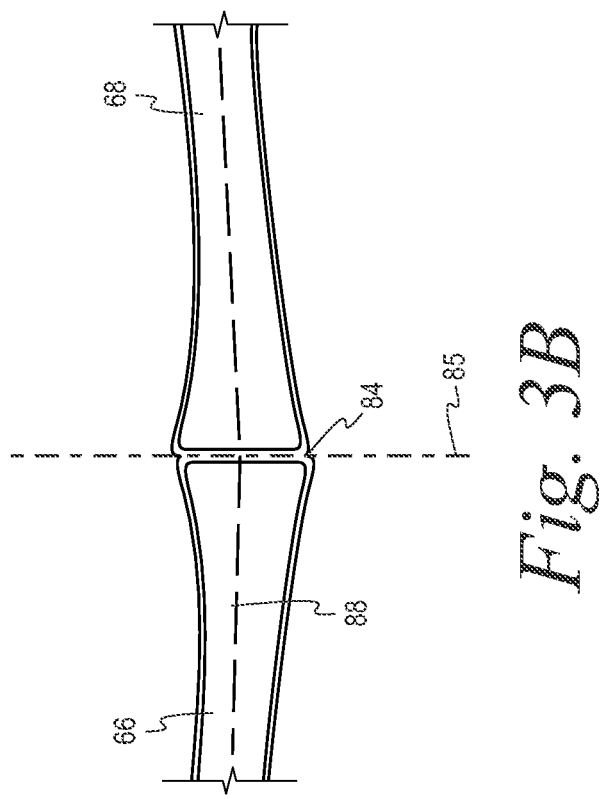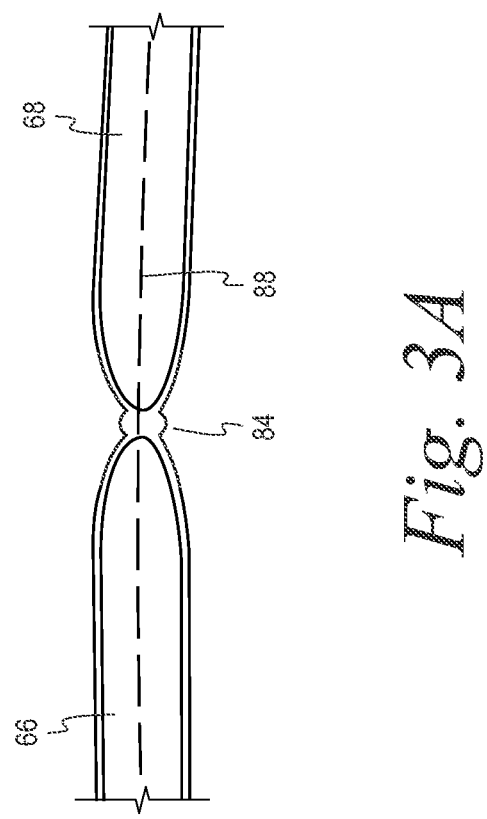

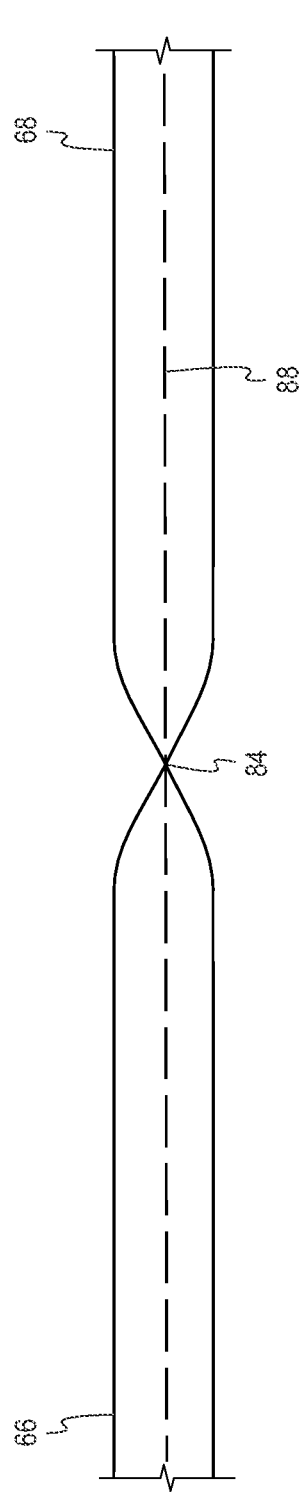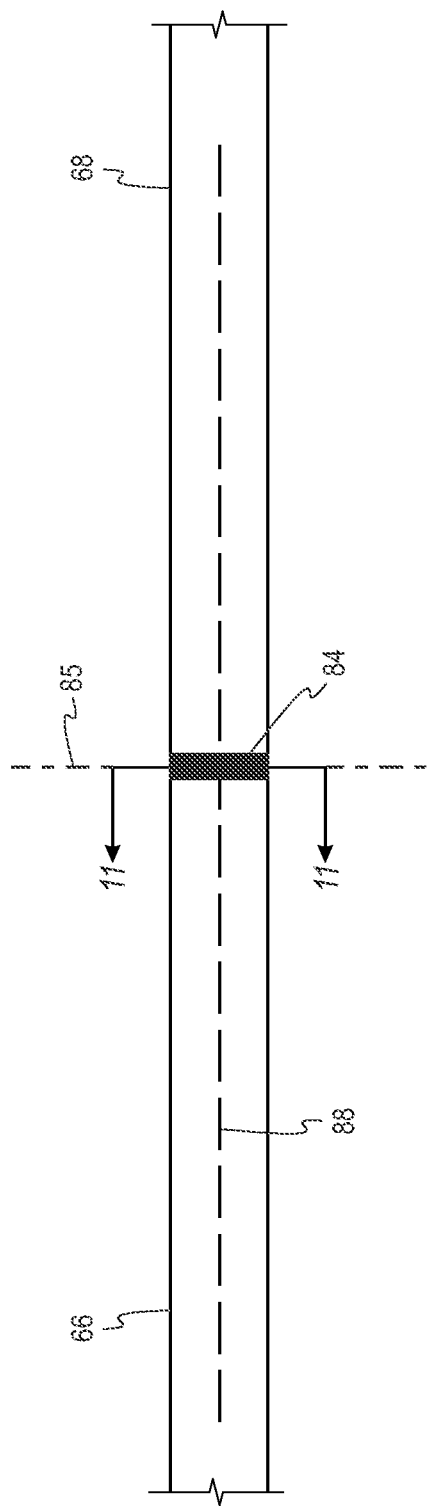

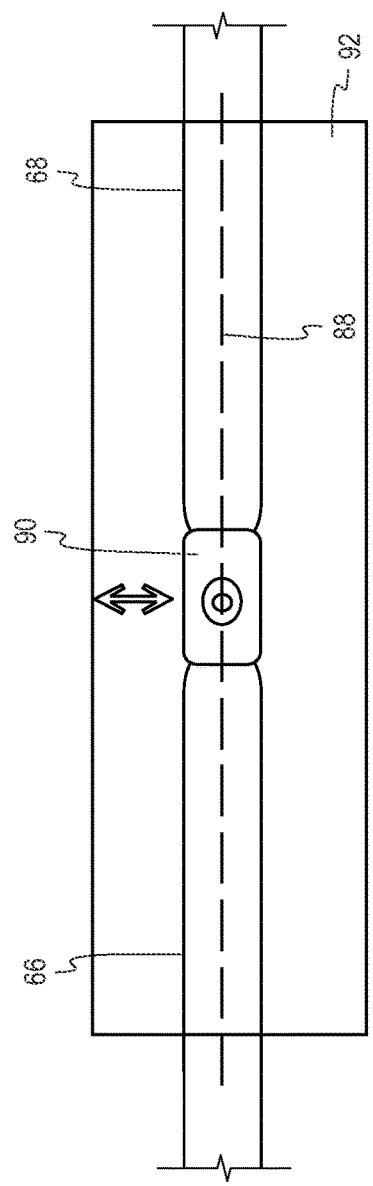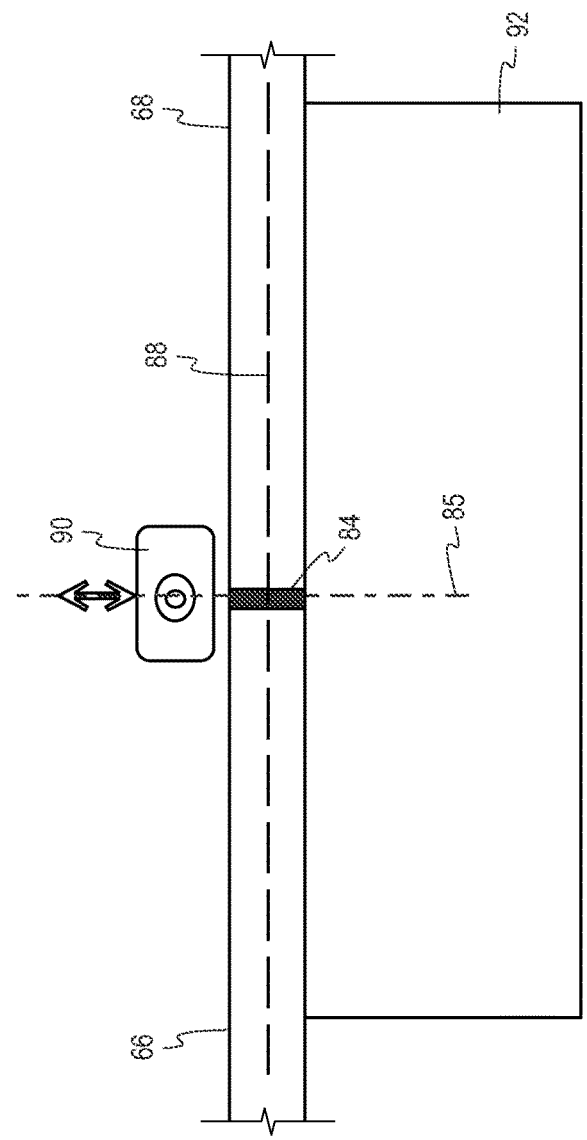

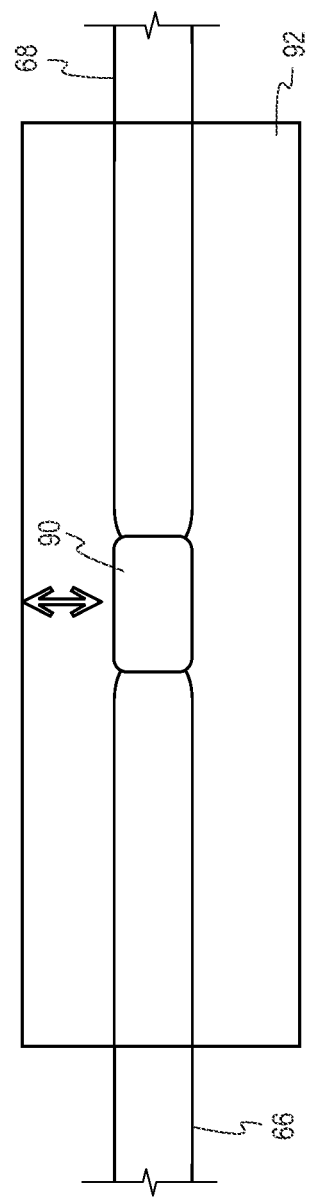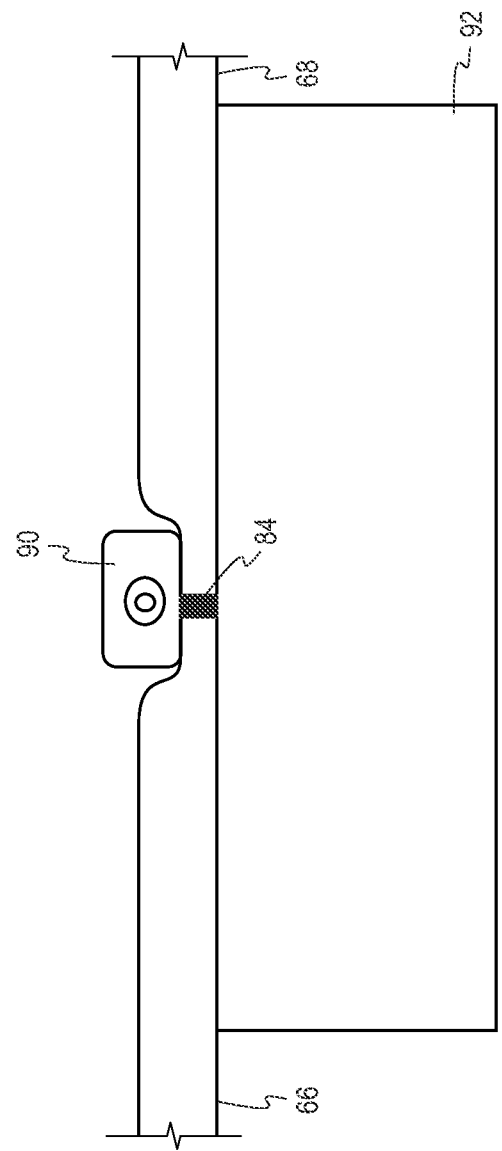

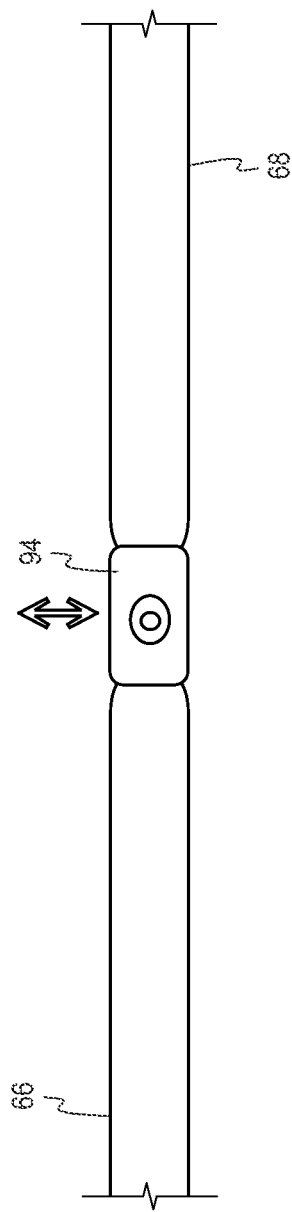
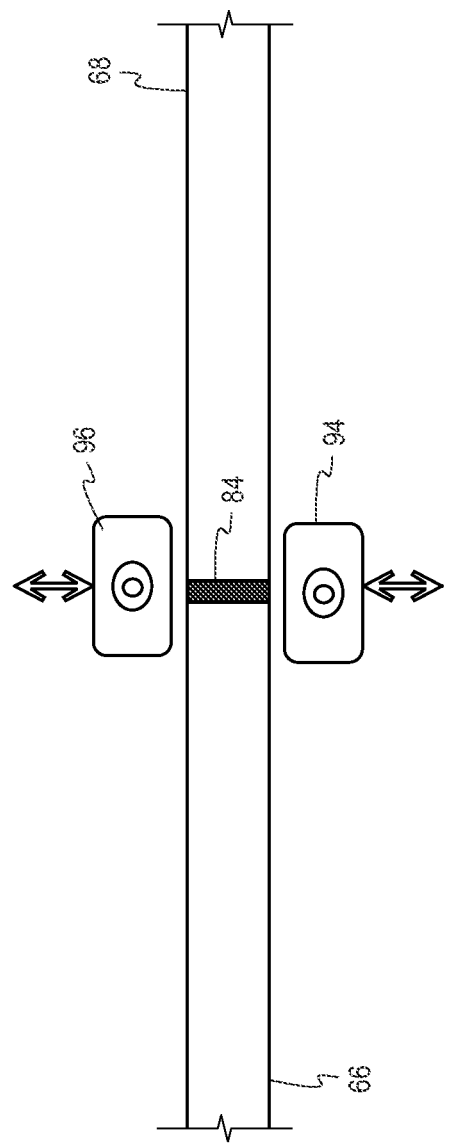

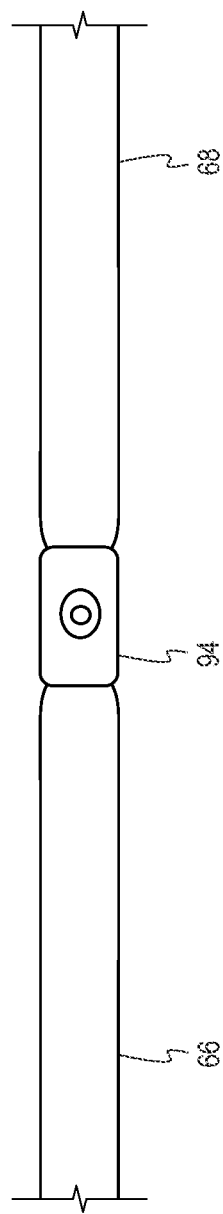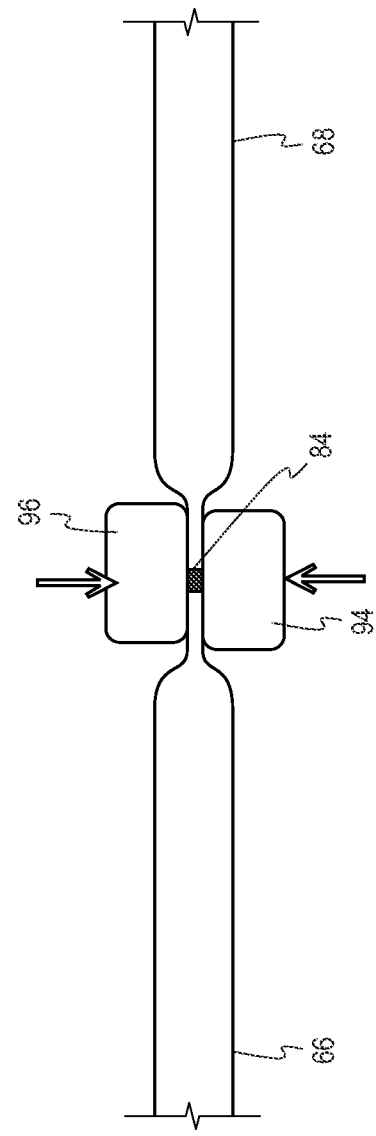

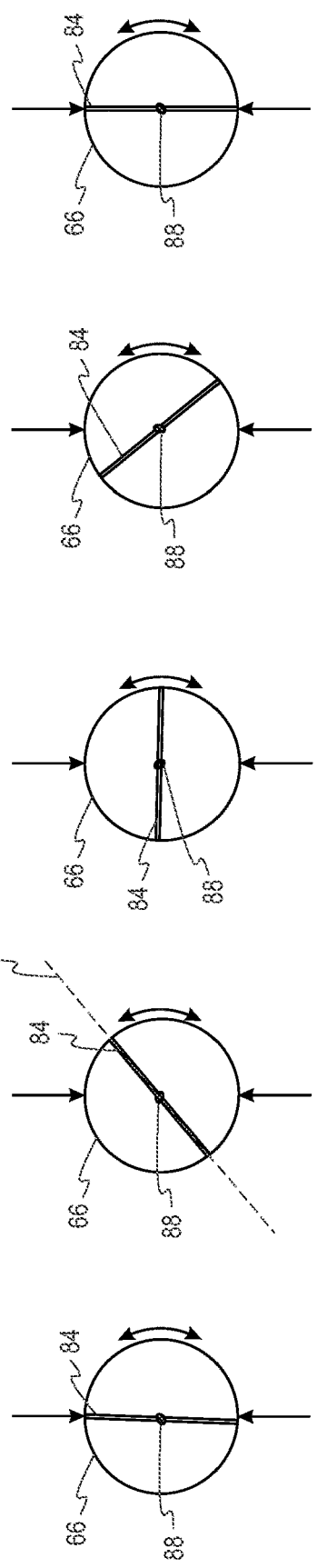

APPARATUS AND METHOD FOR MECHANICALLY OPENING A CONNECTION SITE

This application claims priority to and the benefit of U.S. Provisional Patent Application No. 62/516,214, filed Jun. 7, 2017, which is hereby incorporated by reference in its entirety.

BACKGROUND

The present disclosure generally relates to apparatus and methods for opening a connection site between two flexible thermoplastic conduits, such as, for example, a sterile connection site in fluid flow tubing in a medical fluid flow circuit employed in collecting, processing or treating medical fluid such as blood or blood components.

It is well known in the medical industry in general and particularly in the blood banking field to use connection systems for connecting two separate tubing segments of a fluid flow set or circuit in a manner that prevents the introduction of contaminants or preserves the sterility of the tubing, if pre-sterilized, during the connection process. Such systems have found application both in the large scale assembly or manufacture of fluid flow circuits and in the hands of the ultimate user for on-site assembly of fluid flow circuits having a desired configuration. For example, a user may desire to carry out a particular medical procedure, such as for collecting, processing or treating blood and blood components. These connection devices or systems are commonly referred to in the medical field as sterile connection or sterile docking devices.

Known connection devices or systems include electron beam systems, as in U.S. Pat. No. 5,009,645; radiant energy systems that melt facing membranes of fluid flow conduits, as in U.S. Pat. No. 4,157,723, and heated wafer systems that employ expensive wafers for cutting and heating tubing segments that are bonded or spliced together while the ends remain at a molten or semi-molten elevated temperature, such as in U.S. Pat. Nos. 4,753,697, 5,158,630, 5,156,701 and 5,279,685.

More recently, a novel rotary connection system and apparatus has been described that connects flexible thermoplastic tubing segments by heat or melt bonding the ends together while the ends are individually clamped into a closed position, preventing ambient contamination. Such a system, which does not require the use of heated wafers, is described in detail in U.S. patent application publication no. 2013/0153048, which is incorporated by reference herein in its entirety.

The connection made by heated wafer systems as well as by the wafer-free apparatus described above may have a temporary closed condition or crimped shape due to the high temperature and clamping of the tubing segment ends during connection. More specifically, as a result of the particular connection process, a portion of thermoplastic material from the tubing, also referred to as a "skin", "membrane" or "web," may close or reduce the size of the lumen between the tubing segments. In other words, after the connection is made, the tubular segments remain crimped or stuck together at the connection site, and the cross section of the tubular segments is reduced or flattened along a seal line between the tubing segments. This thermoplastic blocking portion of the connection can be broken or otherwise disrupted to open the lumen for fluid flow between the tubing segments by light external pressure or manipulation, including manual or mechanical manipulation, at the connection point or site. Examples of mechanical manipulation may be found in, for example, U.S. Pat. Nos. 4,610,670; 4,619,642 and 5,674,333 and EP No. 0599057 B1 and WO 2011144561 A1. U.S. Pat. No. 9,533,135 shows the use of gas pressure or vacuum to open a connection site.

The subject matter of this description relates to an apparatus and method to automatically break or otherwise disrupt the thermoplastic skin or web and therefore more fully open such a connection site and the lumen of the tubing segments to allow or improve fluid flow between the connected tubing segments.

BRIEF DESCRIPTION OF DRAWINGS

Turning now to a more detailed description of the present subject matter, which is presented for purposes of description and not limitation, various aspects and features of the present subject are seen in the attached drawings, of which:

FIGS. 3A and 3B are views, taken at different angles, of two thermoplastic tubes or tubing segments heat bonded or welded together by apparatus and method similar to that shown in FIGS. 1A-1C. For consistent reference purposes only, FIG. 3A is referred to as a top view and is generally parallel to the connection site seal line formed by the crimping action of the sealing or welding apparatus. The viewing angle of FIG. 3B is generally orthogonal to that of FIG. 3A. FIG. 3B is referred to as a side view, and the viewing angle is generally perpendicular to the connection site seal line formed by the crimping action of the connection sealing or welding apparatus.

FIGS. 4A and 4B are, respectively, diagrammatic line drawings of the tubing segments of FIGS. 3A and 3B, and are employed in later figures to illustrate the structure and function of apparatus and method described herein for disrupting the web or skin blocking fluid flow through the connection site after welding of the tubing or tubing segments together and opening the fluid flow lumen therethrough.

FIGS. 5A and 5B are, respectively, diagrammatic line drawings of the tubing or tubing segments of FIGS. 3A and 3B, showing the connection site located between a platform and a plate or roller in a first spaced apart position for receiving the tubing segment connection site therebetween.

FIGS. 7A and 7B are similar to the FIGS. 6A and 6B, and also illustrate a direction of relative motion as between the opposed platform and plate or roller for rotating or pivoting the connection site about the longitudinal axis of the tubing or tubing segments, which passes through the connection site located therebetween.

FIGS. 8A and 8B illustrate a further embodiment and are, respectively, diagrammatic line drawings of the tubing segments of FIGS. 3A and 3B, showing the connection site located between opposed plates or rollers in a first spaced apart position for receiving the tubing segment connection site therebetween.

FIGS. 9A and 9B are similar to the FIGS. 8A and 8B, but with the opposed plates or rollers shown in a second closer position for applying pressure to the connection site located therebetween.

FIGS. 11A-11E are cross sectional views of FIG. 4B, taken along line 11-11 through the connection site, and diagrammatically illustrating the tubing or tubing segments and connection site rotated at different angles between the compressive forces applied by opening apparatus as described herein.

BRIEF SUMMARY OF DISCLOSURE

Figure 1A:
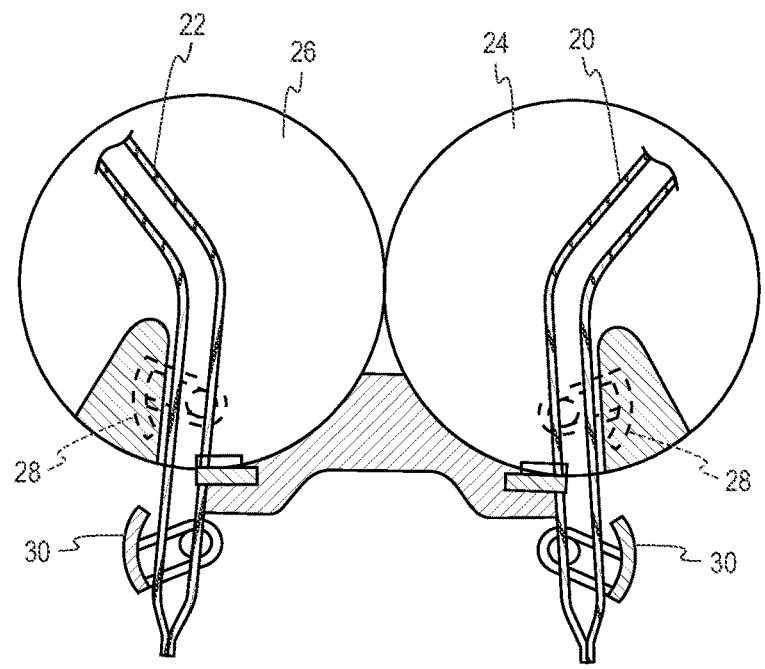
FIGS. 1A-1C show, for background purposes, an embodiment of the device and method for forming a heat-bonded connection described in the above-cited U.S. published patent application publication no. 2013/0153048, which is incorporated herein by reference.

The following is a summary of various embodiments and/or aspects of the present subject matter and is not intended to include every embodiment or aspect or to provide a more detailed description, which may be found in the later detailed description.

In accordance with the present subject matter, apparatus and method are provided for opening or reducing blockage of a welded or heat-bonded connection formed between two hollow, flexible, thermoplastic lengths of tubing or tubing segments, which connection includes a portion of thermoplastic material at least partially blocking internal communication between the conduits. As used herein "reducing the blocking," does not require that the entire blockage be completely removed, but that the amount of blockage is reduced so that flow or enhanced flow (which may differ significantly in different applications) is provided through the connection site between the tubing segments. "Tubing," tubing extension" and "tubing segment" are used interchangeably.

The present subject matter may be used in a stand alone device for opening tubing connection sites or may be employed in combination with apparatus that forms the welded or heat bonded connection between the two tubing segments, such as that described in U.S. published application, publication no. 2013/0153048, or other connection devices. The present subject matter may also be part of or employed in a larger blood processing apparatus that includes, for example, pumps, valves, optional blood separation devices and the like for processing blood or blood components or other medical fluids through a disposable medical fluid flow system, either simultaneously as the blood or blood components are collected from a donor or patient or during post-collection processing (without connection to a donor or patient) of previously collected blood or blood components. Such processing apparatus may also optionally include apparatus for forming a heat bonded connection site between thermoplastic tubing segments of such a medical fluid flow system. As used herein, "blood" is intended to include whole blood and blood components such as plasma or concentrated red cells, either with or without other blood components or added liquids such as anticoagulant, and "medical fluids" is intended to have a comprehensive definition to include all of the above and any other biological, medicinal, therapeutic, diagnostic or medical treatment fluid or fluid employed in a medical processor.

In accordance with a first aspect of the present subject matter, the connection opening system may be provided as part of a larger connection system or apparatus that includes, without limitation, apparatus for forming a welded connection between thermoplastic tubing segments. In this aspect, the larger connection apparatus or system may comprise (1) a connection forming station employing apparatus for forming a heat-bonded connection site between two hollow, flexible, thermoplastic segments of a medical fluid flow path, the joined tubing segments having a longitudinal axis extending through the heat-bonded connection site (referred to as the connection site axis), and (2) a connection site opening station for opening the heat-bonded connection site. The connection site opening station, as described herein, may include two facing surfaces that can be spaced apart sufficiently to receive the two segments and the heat bonded connection site between the facing surfaces, the facing surfaces being relatively movable to rotate the connection about the connection site axis and preferably simultaneously apply force to the connection site substantially perpendicular to the connection site axis.

In accordance with another aspect, the connection opening system may be provided as a separate or free-standing device for opening a heat-bonded connection site between two hollow, flexible, thermoplastic tubing segments of a medical fluid path. The connection opening system of this aspect may include a connection site opening station comprising at least two facing surfaces; the facing surfaces being relatively movable to a spaced apart position where they are spaced sufficiently to receive the heat bonded connection site between the facing surfaces; and the facing surfaces being relatively movable to rotate the connection about the connection site axis and, preferably simultaneously, apply force to the connection site substantially perpendicular to the connection site axis.

In accordance with a further aspect, the connection opening system may be provided as part of a durable blood processing apparatus operable to process blood or blood components through a disposable medical fluid flow system. Such a durable blood processing apparatus may include one or more pumps or valves for controlling flow of blood or blood components through the disposable medical fluid flow system and a connection site opening station for opening a heat-bonded connection site formed between thermoplastic tubing segments of the medical fluid flow system. The connection site opening station may include at least two facing surfaces that can be spaced apart sufficiently to receive the two segments and the heat bonded connection site between the facing surfaces, the facing surfaces being relatively movable to rotate the connection about the connection site axis and, preferably simultaneously, apply force to the connection site substantially perpendicular to the connection site axis. Such a durable processing device may also include apparatus for making or forming the heat bonded connection between tubing segments.

In accordance with yet another aspect, a method of opening a heat-bonded connection may be provided employing any of the systems or apparatus of the above aspects or in the additional aspects set forth below.

Further aspects of the present subject matter or that may be employed with the present subject matter are set forth below.

DETAILED DESCRIPTION

Figure 1B:
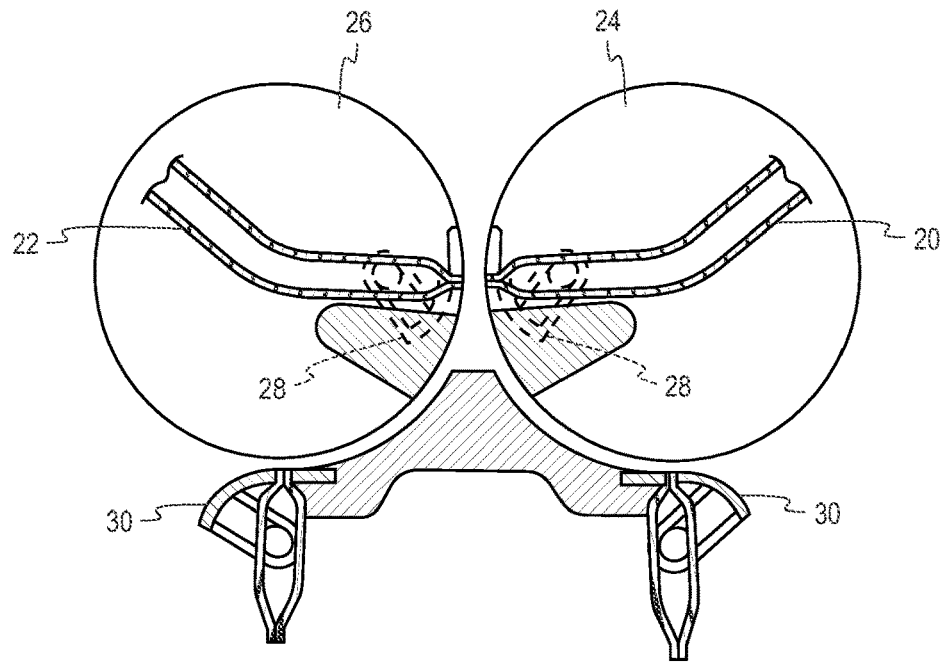
Figure 1C:
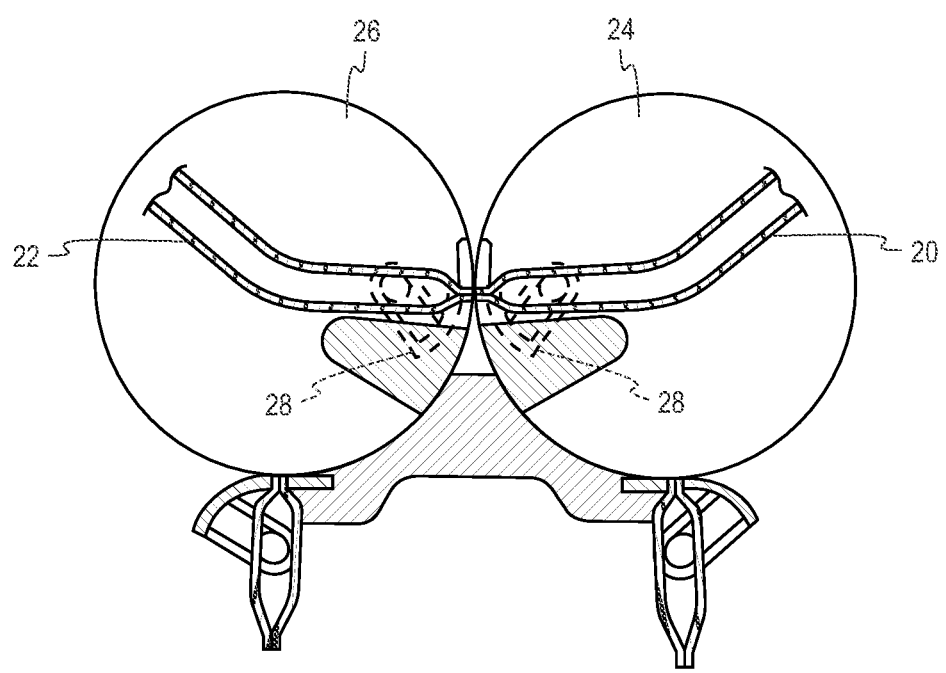

Turning now to a more detailed description, the attached drawings are provided for purposes of illustration and not limitation. As noted earlier, the present subject matter is particularly useful in opening a heat or melt bonded or welded connection site formed by connection devices such as, but not limited to that illustrated in U.S. published patent application publication no. 2013/0153048. FIGS. 1A-1C are taken from that application and illustrate, for background and description purposes, one example of a prior device and method for forming a heat-bonded (also referred to interchangeably as "melt-bonded" or "welded") connection between two flexible thermoplastic conduits or tubes.

Illustration of this particular device does not imply that the present subject matter is useful only with heat or melt bonded connections formed by such device. Connections formed by other apparatus may also be used with the present subject matter. Without unduly elaborating on the details of the device and method shown in the above application, which are fully explained in the published application, sealed thermoplastic conduit tubing or tubing segments 20 and 22 are each received on a rotatable disc, respectively 24 and 26. Each disc cooperates with two pair of clamping jaws 28 and 30, one of which may also be a high frequency voltage electrode for heating the clamped tubing. As seen in FIG. 1B, after the tubing segments are clamped and heated, the discs shift laterally to separate the clamping jaws and rotate to the positions seen in FIG. 1B. This exerts a tensile and shear force on the tubing segments, such that each tubing segment is separated from the sealed end portion of that segment. Because the clamping jaws 28 keep the ends of the segments clamped and sealed, sterility of the segments, if pre-sterilized, is maintained and, in any event, the tubing segments are safeguarded from introduction of ambient bacteria or microorganisms.

After the tubing segment ends are brought into a facing position by rotation of the discs, as shown in FIG. 1B, the discs move laterally again, bringing the tubing segment ends into direct contact. Because this happens while the tubing ends are still at elevated temperature and in semi-molten state, they form an integral, welded bond or heat-bonded connection site (better seen as connection site 84 in FIGS. 3A, 3B, 4A and 4B). Because the process may result in a thermoplastic portion or "skin" blocking communication between the lumen of the joined conduits or tubes (see FIGS. 3A, 3B, 4A and 4B), after cooling, manual manipulation may be employed to break the skin and open the connection between the tubing segments for fluid flow. The present subject matter, as described below, avoids the need for manual manipulation.

Figure 2:
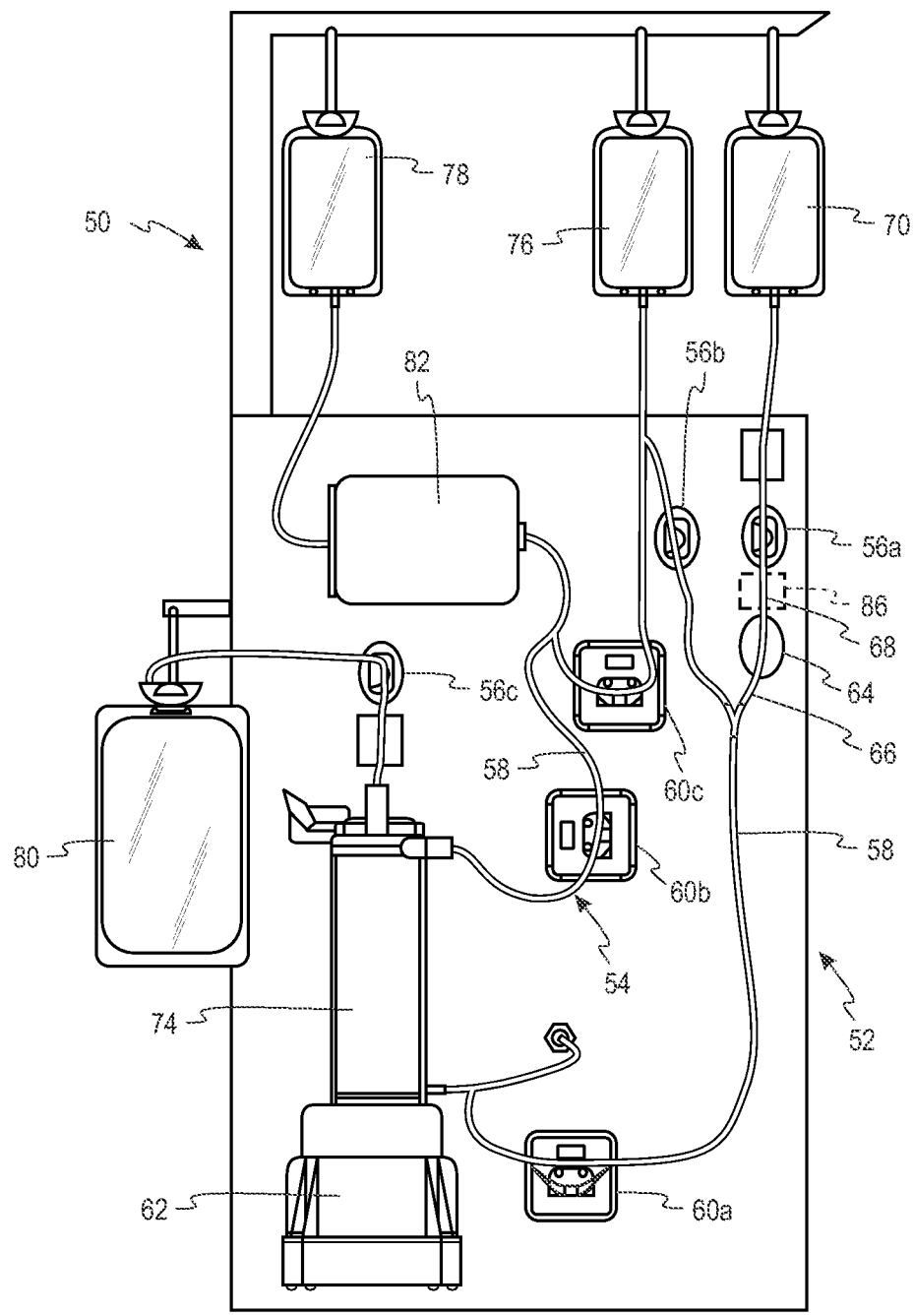
FIG. 2 is an elevational view of a fluid processing system depicting how the present subject matter maybe employed as part of a durable apparatus for processing blood, blood components or other biological or other medical fluids. The present connection opening apparatus and method also can be free-standing in a separate device or as part of other apparatus, such as connection apparatus that includes apparatus for forming a heat-bonded connection site.

FIG. 2 shows one embodiment that serves to illustrate the use of the present connection site opening apparatus and methods summarized above, as part of a larger fluid processing system. The system shown is for purposes of illustration and not limitation to the features of the particular system shown. More specifically, FIG. 2 depicts a medical fluid processing system, generally at 50, for processing medical fluid such as blood, including blood collected from a donor. The system includes a reusable, durable processing device 52, upon which a disposable, one-time use fluid flow circuit 54 may be mounted. The illustrated durable device includes, as necessary, valves or pumps for cooperating with the fluid flow circuit to control the flow of blood, blood components and other liquids through the circuit and carry out the desired processing. Depending on intended use, the durable device may optionally also include sensors, hangers, scales, drive systems, separation devices and the like.

The disposable fluid flow circuit 54 is, at least in part, preassembled and pre-sterilized, and may be made up of fluid flow tubing, and any desired containers and processing devices that may be assembled onto the durable device for conveying blood, blood components and/or other associated fluids through the fluid processing circuit without introducing extraneous materials or contaminants. Only the disposable, one-time use fluid flow circuit contacts the blood or other liquids, thus avoiding the need to sterilize the durable hardware components and significantly reducing administrative burdens and costs associated with the processing.

As illustrated, the durable portion of the system may include, among other things, one or more flow control valves 56*a-c* for assisting in controlling flow through flexible plastic tubing 58 of the fluid flow circuit 54. Typically, each valve includes a pair of clamping or pinching jaws, between which fluid flow tubing of the fluid flow circuit is placed when the flow circuit is assembled onto the face of the device 52. The valves close or open the tubing in response to commands from the operating control system of the device 52 based on the particular process selected by the user. Typically, but not exclusively, the control system for device 52 employs a programmable microprocessor based controller that allows the device to be configured for one or more of different selected procedures for processing blood, blood components or other biological or medical fluids. In the present description, the system is shown, for illustrative purposes only, for processing a unit/container of previously whole blood collected from a donor, for example in a prior collection procedure. The whole blood may be processed, for example, to separate it into concentrated red cells, plasma and platelets, each of which finds application in particular medical situations, thus resulting in more efficient usage of the collected blood. The present subject matter may also be used in connection with a disposable fluid flow circuit and durable device that processes blood collected while the donor or patient is attached to the device.

The durable device 52 may also include optionally one or more pumps 60*a-c*, such as peristaltic type pump, operable on the tubing 58 of the fluid flow circuit to direct flow therethrough. In addition, the durable device may also optionally include a station 62 for receiving and interacting with a blood separation device, and various other sensors, weigh scales and other components to control fluid processing through the fluid flow circuit. For example, the disposable fluid flow circuit 54 illustrated in FIG. 2 may include, for example, a blood separation device 74, one or more containers or bags 76 (e.g., containing RBC additive solution), 78 (e.g., for receiving concentrated RBCs) and 80 (e.g., for receiving plasma), leukoreduction filter 82 and associated flexible tubing 58 connecting the various components in a fluid flow relationship. The preassembled circuit may be pre-sterilized, and the tubing extensions or tubing segments 66 and 68 may, before joinder, terminate at a heat sealed end to preserve sterility.

When mounted on the illustrated durable device, the components of the preassembled flow circuit are placed on or in their selected locations, for example, the blood separation device 74 in the station 62, the tubing in the valves 56, sensors, and pumps 60 and the bags 76-80 on the various hangers. To carry out the illustrated blood processing, a bag of pre-collected blood 70 is suspended from the appropriate hook or hanger and tubing segments 66 and 68 of the fluid circuit, are placed in operative position on a connection forming apparatus, generally at 64, as illustrated in more detail in FIGS. 1A-1C—which may include apparatus such as but not limited to that described in U.S. published application publication no. 2013/0153048, for forming a heat-bonded connection, such as a sterile connection, between tubing segments that are joined to form part of the disposable fluid flow circuit.

Before turning to further details of the present opening method and apparatus, it should be noted that it is not required, either for the connection forming apparatus 64 of the above published application or for the subject matter described herein, that the conduits to be of exactly the same size or material, although the material and size should be sufficiently compatible as necessary to form the heat-bonded connection. It is contemplated for application in medical fluid flow circuits that the tubing or tubing segments will typically be flexible tubing of polyvinyl chloride ("PVC") or other flexible thermoplastic material, with an interior lumen for flowing medical fluids such as blood, blood components, anticoagulant, saline, or other liquids. In a typical fluid flow circuit for collecting, processing or treating blood or blood components, such as the type marketed by Fenwal Inc., of Lake Zurich, Ill., the fluid flow tubing may be hollow PVC tubing, a flexible thermoplastic material, having an internal lumen diameter of about 0.118-0.126 inches (3-3.2 mm) and a wall thickness of about 0.025-0.03 inches (0.635-0.762 mm). As noted above, however, this subject matter is not limited to a particular size or material for the conduits.

In the illustrated embodiment, the connection formed is between a flexible thermoplastic (PVC) tubing segment 66 of the preassembled disposable fluid circuit 54 and flexible thermoplastic (PVC) flow tubing segment 68 attached to a container or bag 70 of collected blood, although it is not necessarily attached to a bag or container.

As explained earlier, when the connection between the tubing segments is formed by the connection apparatus 64, a thermoplastic portion or skin may be formed during the connection process and blocks or reduces flow through the tubing segments 66 and 68. In that condition, the tubing segments may appear substantially as show in FIGS. 3A and 3B, with the tubing wall compressed together and held by a plastic web or skin at the connection site 84, as best seen in "top view" of FIG. 3A, and the heat bonded connection being in the form of or extending in a line 85, which is oblique or transverse to the longitudinal axis (i.e., the connection site axis 88) of the tubing, as best seen in the "side view" of FIG. 3B.

As explained earlier, the present subject matter is directed to apparatus and method for disrupting the connecting web or skin of thermoplastic material and automatically opening the heat bonded connection site 84 as shown, for example, in FIGS. 3A and 3B. Although described in part with respect to a blood processing device 52, to be abundantly clear, the opening apparatus and method described herein may be employed in any suitable arrangement, and this description is by way of example only and not limitation. For example, the opening apparatus and method described herein may be configured as an entirely separate device for the sole purpose of opening heat bonded connection sites; or it may be employed in combination with apparatus for forming the heat bonded connections as part of a device that is devoted to forming and opening heat bonded connections and is separate from any larger blood processing system; or it may be employed alone or in combination with connection forming apparatus on a larger fluid processing device for processing blood, blood components, other biological or medical fluids; or it may be employed in any other desired application or arrangement.

For purposes of illustration only, in FIG. 2 the connection site opening apparatus is shown diagrammatically on the face of the durable device, and generally referred to as opener 86. The opener 86 may be located at a convenient site on the processing device 52 to allow the tubing segments and connection site to be manually or automatically moved from the connecting apparatus 64 to the opener 86.

The tubing or tubing segments 66 and 68, the connection site 84 and the opener 86 and method for opening the connection site are shown more fully in FIGS. 3A-10B. For purposes of describing the connection site opening method and apparatus herein, reference may be made to the longitudinal axis 88, shown in FIGS. 3A and 3B, that extends axially through the lumen or bore of tubing segments 66 and 68 and passes through the seal line 85 at the connection site 84. This axis will be referred to at the connection site axis.

When the heat bonded or welded connection site is formed, associated clamps typically compress or clamp the tubing segments in proximity to connection site, resulting in a physical appearance of the connected tubing segments 66 and 68 as seen in FIGS. 3A and 3B, wherein the connection site, before opening, extends along a line 85 that may be transverse or orthogonal to the connection site axis 88. FIG. 3A shows the compressed tubing segments 66 and 68 when looking at an end edge of the connection site line. FIG. 3B is from a viewing angle 90 degrees from the viewing angle of FIG. 3A, and shows the connection site line 85 along its length, and the outward flaring of the tubing segments at the connection site as a result of the jaws that clamp the tubing during the formation of the connection site. Because of the connection forming process the compressed walls of the tubing segments tend to stick together along the connection or bonding site line 85, thus blocking or reducing flow between the tubing segments.

FIGS. 4A and 4B show the tubing segments 66 and 68 and connection site 84 of FIGS. 3A and 3B diagrammatically as line drawings, and will be employed in the discussion below to better illustrate the opening apparatus and method. Further, for consistent reference purposes, FIG. 3A and similar line drawings viewing the connection site seal line 85 from an end or edge view are labeled 3A, 4A, 5A etc. and are referred to as the top view, and FIG. 3B and similar line drawings showing the length of the connection site seal line 85 are labeled 3B, 4B, 5B etc. and are referred to as the side view. It is thus apparent that the top and side views are taken orthogonally, at 90 degrees, relative to one another.

The opening method and apparatus as described below employs at least two facing surfaces of any suitable shape or configuration, between which the connection site 84 can be positioned. The surfaces are relatively movable by any suitable means (not shown), such as a motor or solenoid or other mechanical, electrical, pneumatic or hydraulic drive, to rotate the connection site about the connection site axis 88 and to apply force to the connection site that is substantially perpendicular to the connection site axis 88, compressing the connection site as it is rotated or pivoted. Preferably, but not necessarily, the compressive force is applied simultaneously with the rotation. The connected tubing segments 66 and 68 may be rotated about the connection site axis 88 without moving in another direction or may also translate in another direction, such as laterally or at a right angle to the connection site axis, while being rotated. The rotation results in the surfaces periodically applying a compressive force against the end edges of the connection site seal line 85 (e.g., twice during each 360 degrees of rotation as illustrated in FIGS. 11A and 11E), which tends to help open the connection site and to reshape the connection site into a rounded instead of a flattened condition to allow fluid flow between the tubing segments. The relative movement of the surfaces may be in the same direction or in opposite directions or may also be reciprocating, so that the connection site is rotated in one direction and then in a reverse direction, in a "back and forth" manner to repeatedly apply compressive force to the ends of the connection site seal line. The amount of rotation induced by relative movement of the surfaces may be fixed or variable. For example, the connection site may be rotated about the connection site axis a fixed amount of about 180-720 degrees, such as 180-360 degrees in one direction or, if the relative movement is reciprocating, the amount of rotation could be the same or variable in opposite directions. As a further example, the connection site could be rotated a first amount in one direction and then a greater or lesser amount in the opposite direction. Similarly, the amount of pressure/force applied by the surfaces may vary, such as increasing or decreasing or alternately increasing and decreasing. This may be continued until the connection site is opened, which may be confirmed visually, tactilely or automatically such as by sensing internal pressure variation within the tubing segments.

Turning now to FIGS. 5A and 5B, illustrated there is an arrangement in which one of the surfaces is the surface of a plate or roller 90 and the other surface is the facing surface of a facing platform 92. FIGS. 5A and 5B show the respective surfaces spaced apart sufficiently to allow at least the connection site 84 to be positioned between them. In this arrangement, the platform is relatively stationary and the roller or plate has two degrees of freedom, being movable toward and away from the platform surface as reflected by the arrow in FIG. 5B so as to exert a force against the end edges of the connection site 84, and movable from side to side or laterally relative to the platform surface as indicated by the arrow in FIG. 5A, so as to cause rotation of the tubing segments. Alternatively, the platform 92 could be movable and the plate or roller 90 stationary, or they could both be movable.

Figure 6A:
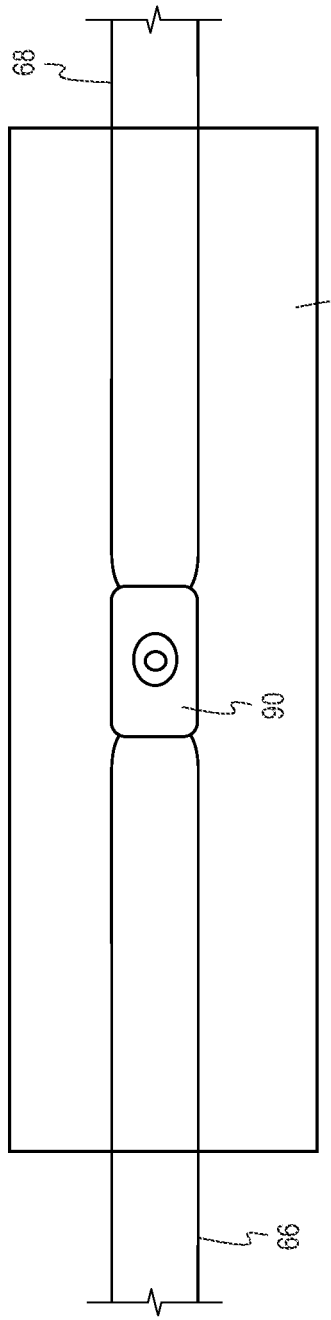
FIGS. 6A and 6B are similar to the FIGS. 5A and 5B, but with the platform and plate or roller shown in a second closer position for applying pressure to the connection site located therebetween.
Figure 6B:
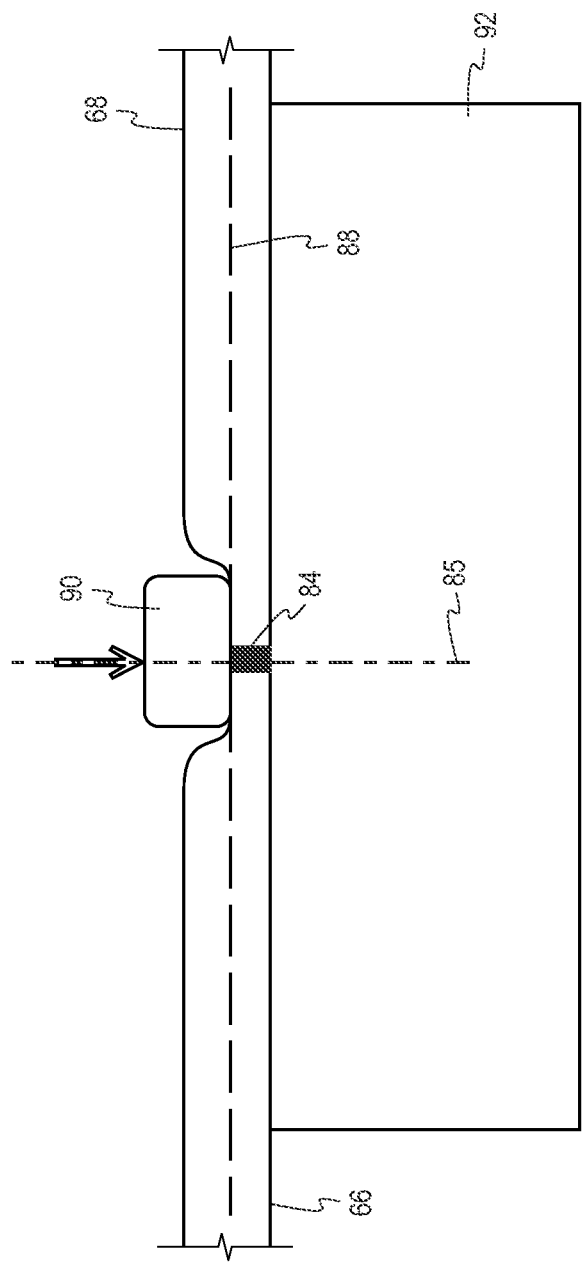

FIGS. 6A and 6B show the roller or plate 90 moved to a closer position relative to the platform 92, applying a compressive force against connection site 84 and specifically against the end edges of the connection site seal line 85, squeezing the ends toward one another. In other words, the compressive force is generally perpendicular to the connection site axis 88 and parallel to the connection site seal line 85 as seen in 6B. The roller or plate 90 would then be moved laterally, parallel to the surface of platform 92, as described below.

FIGS. 7A and 7B show the system of FIGS. 5 and 6, illustrating lateral movement, such as reciprocating movement, of the plate or roller 90 relative to the platform 92 as indicated by the arrow in FIG. 7A. The movement may be described as parallel to the plane of the page in FIG. 7A and into or out of the page in FIG. 7B. The lateral movement of the plate or roller while contacting and compressing the connection site 84 causes the connection site and tubing segments to rotate or pivot about the connection site axis, applying force to the connection site from various directions, as illustrated in FIG. 11A-11E. This causes deformation of the connection site from the flattened connection immediately after the connection is formed (see FIGS. 3A and 3B) to a more rounded condition, disrupting the blocking web or skin of the seal or weld between the opposed walls of the tubing segments, while leaving intact the connection between two tubing segments 66 and 68, and opening the connection site to fluid flow between the tubing segments. While the opposed surfaces are illustrated here as the surface of the platform 92 and the surface of the roller or plate 90, it should be understood that other suitable shapes or configurations could be used that can achieve compression and rotation of the connection site.

FIGS. 8A and 8B show an alternative embodiment, similar to FIG. 5, but illustrating the connection site 84 between opposed surfaces in the form of facing plates and/or rollers 94 and 96, each of which has two orthogonal degrees of freedom of movement. Both opposed surfaces could be in the form of plates or rollers or one could be a plate and one a roller or other shapes could be used to achieve that are suitable to exert the needed force on the connection site and to impart rotation of the connection site. As shown in FIG. 8B, as depicted by the arrows, each plate or roller is relatively movable toward and away from the other (parallel to the surface of the page) to compress the connection site in an end to end direction, although only one could be movable. As indicated by the arrow in FIG. 8A, both of the plates or rollers also are also laterally movable relative to one another to apply compressive force to the connection site, although this also could be varied. FIGS. 8A and 8B show the facing plates or rollers in a spaced apart position to allow positioning of the connection site therebetween.

FIGS. 9A and 9B show the rollers or plates 94 and 96 after they moved to a closer position, applying a compressive force against connection site 84 and particularly against the end edges of the connection site seal line 85 such that the direction of the force is substantially parallel to the seal line of the connection site. In other words, similar to FIG. 6, the compressive force exerted on the connection site is generally parallel to the connection site seal line 85 and perpendicular to the connection site axis 88.

Figure 10A:
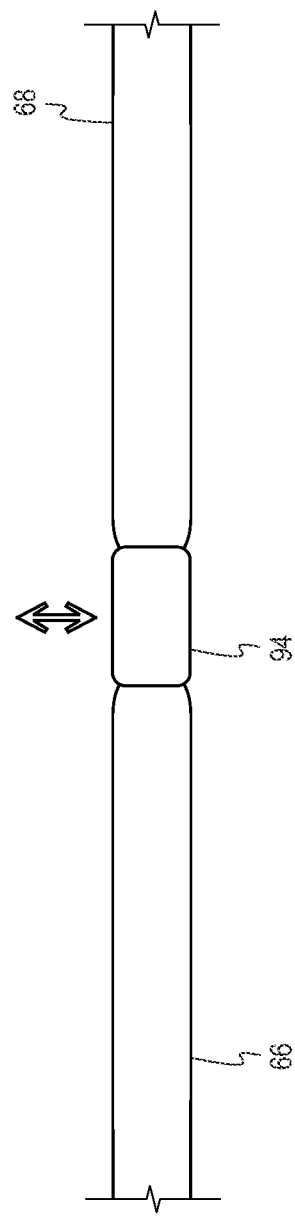
FIGS. 10A and 10B are similar to the FIGS. 9A and 9B, and also illustrate a direction of relative motion as between the opposed plates or rollers for rotating the connection site about the longitudinal axis of the tubing or tubing segments, which passes through the connection site located therebetween.
Figure 10B:
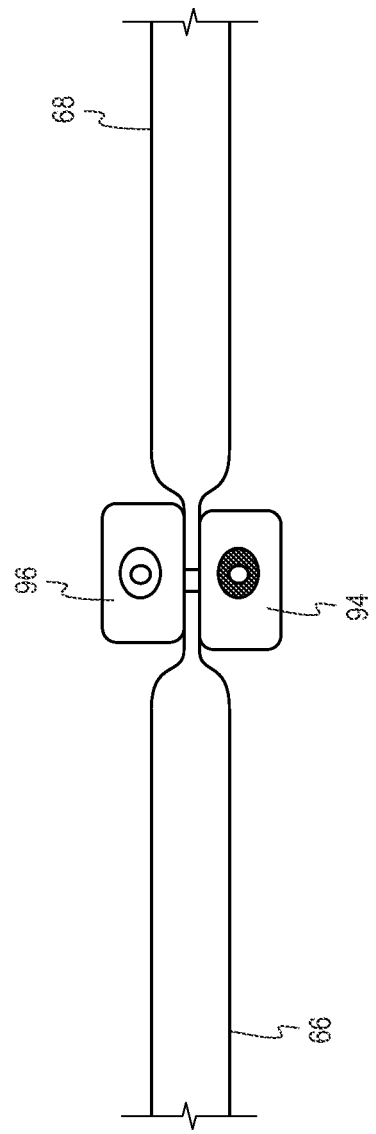

FIGS. 10A and 10B show the system of FIGS. 8 and 9, illustrating lateral movement of the plates or rollers 94 and 96 relative to each other after application of force against the connection site as shown in FIGS. 9A and 9B, as indicated by the arrow in FIG. 10A. In this example, the plates or rollers are movable simultaneously in opposite lateral directions, such that with reference to FIG. 10B plate or roller 94 is illustrated moving in direction into or out of the plane of the paper and plate or roller 96 is also illustrated as moving into or out of the plane of the paper. With reference to FIG. 10A, the movement is parallel to the plane of the page. The relative lateral movement of the plates or rollers while contacting and compressing the connection site 84, as shown in FIG. 10A, causes the connection site and tubing segments to rotate or pivot about the connection site axis, thus applying force to the connection site from various directions, as illustrated in FIG. 11A-11E, as the connection site rotates or pivots. This causes deformation of the connection site from the flattened connection immediately after the connection is formed (see FIGS. 3A and 3B) to a more rounded condition, disrupting the blocking web or skin of the seal or weld between the opposed walls of the tubing segments, while leaving intact the connection between two tubing segments 66 and 68, and opening the connection site to fluid flow between the tubing segments. While the opposed surfaces are illustrated here as the surface of a plate and the surface of a roller or plate, it should be understood as noted earlier that other combinations of rollers and/or plates and other suitable shapes or configurations and different directions of movement could be used that can achieve compression and rotation of the connection site.

Various Additional Aspects

In accordance with a first aspect of the present subject matter, referred to as aspect no. 1, as noted earlier, the connection opening system may be provided as part of a larger connection system or apparatus that includes, without limitation, apparatus for forming a welded connection between thermoplastic tubing segments. In this aspect, the larger connection apparatus or system may comprise (1) a connection forming station employing apparatus for forming a heat-bonded connection site between two hollow, flexible, thermoplastic segments of a medical fluid flow path, the joined tubing segments having a longitudinal axis extending through the heat-bonded connection site (referred to as the connection site axis), and (2) a connection site opening station for opening the heat-bonded connection site. The connection site opening station, as described herein, may include two facing surfaces that can be spaced apart sufficiently to receive the two segments and the heat bonded connection site between the facing surfaces, the facing surfaces being relatively movable to rotate the connection about the connection site axis and preferably simultaneously apply force to the connection site substantially perpendicular to the connection site axis.

In accordance with aspect 2, the connection system of aspect 1 may include one of the facing surfaces being substantially stationary and the other of the facing surfaces being movable with at least two degrees of freedom.

In accordance with aspect 3, the connection system of aspect 1 may include each of the facing surfaces being movable with at least one degree of freedom.

In accordance with aspect 4, the connection system of any one of aspects 1-3 may include at least one of the facing surfaces being substantially cylindrical.

In accordance with aspect 5, the connection system of any one of aspects 1-4 may include at least one of the facing surfaces being generally or substantially planar.

In accordance with aspect 6, the connection system of any one of aspects 1-5 may include at least one of the facing surfaces being movable with at least one degree of freedom in one direction and the other facing surface being movable with at least one degree of freedom in a different direction.

In accordance with aspect 7, the connection system of aspect 6 may include the other facing surface being movable in a different direction that is substantially orthogonal to the one direction.

In accordance with aspect 8, the connection system of any of aspects 1-7 may include one of the facing surfaces being substantially cylindrical and rotatable about its own axis of rotation and the other facing surface being substantially planar and movable in a direction substantially perpendicular to the axis of rotation of the cylindrical surface.

In accordance with aspect 9, the connection system of any one of aspects 1-3 and 5-7 may include each of the facing surfaces being substantially planar and one of the facing surfaces being movable in a direction generally perpendicular to the surface of the other of the facing surfaces, and the second facing surfaces being movable in a direction substantially parallel to the first facing surface.

In accordance with aspect 10, as noted earlier, the connection opening system may be provided as a separate or free-standing device for opening a heat-bonded connection site between two hollow, flexible, thermoplastic tubing segments of a medical fluid path. The connection opening system of this aspect may include a connection site opening station comprising at least two facing surfaces; the facing surfaces being relatively movable to a spaced apart position where they are spaced sufficiently to receive the heat bonded connection site between the facing surfaces; and the facing surfaces being relatively movable to rotate the connection about the connection site axis and, preferably simultaneously, apply force to the connection site substantially perpendicular to the connection site axis.

In accordance with aspect 11, the connection opening system of aspect 10 may include one of the facing surfaces being substantially stationary and the other of the facing surfaces being movable with at least two degrees of freedom.

In accordance with aspect 12, the connection opening system of aspect 10 may include each of the facing surfaces being movable with at least one degree of freedom.

In accordance with aspect 13, the connection opening system of any one of aspects 10-12 may include at least one of the facing surfaces being substantially cylindrical.

In accordance with aspect 14, the connection opening system of any one of aspects 10-13 may include at least one of the facing surfaces being generally planar.

In accordance with aspect 15, the connection opening system of any one of aspects 10-14 may include at least one of the facing surfaces being movable with at least one degree of freedom in one direction and the other facing surface being movable with at least one degree of freedom in a different direction.

In accordance with aspect 16, the connection opening system of aspect 15 may include the other facing surface being movable in a different direction that is substantially orthogonal to the one direction.

In accordance with aspect 17, the connection opening system of any of aspects 10-16 may include one of the facing surfaces being substantially cylindrical and rotatable about its own axis of rotation and the other facing surface being substantially planar and movable in a direction substantially perpendicular to the axis of rotation of the substantially cylindrical surface.

In accordance with aspect 18, the connection opening system of any one of aspects 10-12 and 13-16 may include each of the facing surfaces being substantially planar and one of the facing surfaces being movable in a direction generally perpendicular to the surface of the other of the facing surfaces, and the second facing surfaces being movable in a direction substantially parallel to the first facing surface.

In accordance with aspect 19, as noted earlier, the connection opening system may be provided as part of a durable blood processing apparatus operable to process blood or blood components through a disposable medical fluid flow system. Such a durable blood processing apparatus may include one or more pumps or valves for controlling flow of blood or blood components through the disposable medical fluid flow system and a connection site opening station for opening a heat-bonded connection site formed between thermoplastic tubing segments of the medical fluid flow system. The connection site opening station may include at least two facing surfaces that can be spaced apart sufficiently to receive the two segments and the heat bonded connection site between the facing surfaces, the facing surfaces being relatively movable to rotate the connection about the connection site axis and, preferably simultaneously, apply force to the connection site substantially perpendicular to the connection site axis.

In accordance with aspect 20, the durable blood processing apparatus of aspect 19 may include one of the facing surfaces being substantially stationary and the other of the facing surfaces being movable with at least two degrees of freedom.

In accordance with aspect 21, the durable blood processing apparatus of aspect 20 may include each of the facing surfaces being movable with at least one degree of freedom.

In accordance with aspect 22, the durable blood processing apparatus of any one of aspects 19-21 may include at least one of the facing surfaces being generally cylindrical.

In accordance with aspect 23, the durable blood processing apparatus of any one of aspects 19-22 may include at least one of the facing surfaces being generally planar.

In accordance with aspect 24, the durable blood processing apparatus of any one of aspects 19-23 may include at least one of the facing surfaces being movable with at least one degree of freedom in one direction and the other facing surface being movable with at least one degree of freedom in a different direction.

In accordance with aspect 25, the durable blood processing apparatus of aspect 25 may include the other facing surface being movable in a different direction that is substantially orthogonal to the one direction.

In accordance with aspect 26, the durable blood processing apparatus of any of aspects 19-25 may include one of the facing surfaces being substantially cylindrical and rotatable about its own axis of rotation and the other facing surface being substantially planar and movable in a direction substantially perpendicular to the axis of rotation of the substantially cylindrical surface.

In accordance with aspect 27, the durable blood processing apparatus of any one of aspects 19-21 and 23-27 and may include each of the facing surfaces being substantially planar and one of the facing surfaces being movable in a direction generally perpendicular to the surface of the other of the facing surfaces, and the other facing surface being movable in a direction substantially parallel to the one facing surface.

In accordance with aspect 28, a method of opening a heat-bonded connection may be provided employing any of the systems or apparatus of aspects 1-27.

In conclusion, although the present subject matter has been described with reference to specific devices and methods, this is for the purpose of description and not limitation. It is contemplated, for example, that this subject matter may be used with other devices, systems and methods, and reference should be made to the attached claims for an understanding of the scope of certain aspects of the present subject matter.

The invention claimed is:

1. A method of opening a heat-bonded connection site between two hollow, flexible, thermoplastic segments of a medical fluid path defined by a seal line having a connection site axis, with a connection site opening station comprising a roller having a first substantially cylindrical surface rotatable about a first axis and a plate having a second substantially planar surface facing the first cylindrical surface, one of the roller and the plate being moveable perpendicular to the first axis of the roller between a first position in which the facing surfaces are spaced apart sufficiently to receive the two segments and the connection site between the facing surfaces and a second position in which the facing surfaces apply a force to the connection site substantially in alignment with the connection site axis, the roller being movable laterally back and forth relative to the plate when in the second position, the method comprising:
   a) placing the connection site between the facing surfaces of the connection site opening station;
   b) moving the surfaces to compress the connection site substantially perpendicular to the connection site axis; and
   c) rotating the connection site substantially about the connection site axis.

2. The method of claim 1 in which the compressing and rotating occur simultaneously.

3. The method of claim 1 in which the connection site is rotated in a first direction and then in a second direction.

4. The method of claim 3 in which the connections site is rotated a first amount in the first direction and a second amount in the second direction.

5. The method of claim 4 in which the first amount and second amount are fixed.

6. The method of claim 4 in which the first amount and second amount are variable.

7. The method of claim 4 in which the first amount is different from the second amount.

8. The method of claim 4 in which the first amount is equal to the second amount.

9. The method of claim 4 in which the first amount is less than the second amount.

10. The method of claim 4 in which the first amount is greater than the second amount.

11. A method of forming and opening a heat-bonded connection site between two hollow, flexible, thermoplastic segments of a medical fluid path defined by a seal line having a connection site axis, with a connection system comprising a connection forming apparatus and a connection site opening station, the connection site opening station further comprising a roller having a first substantially cylindrical surface rotatable about a first axis and a plate having a second substantially planar surface facing the first cylindrical surface, one of the roller and the plate being moveable perpendicular to the first axis of the roller between a first position in which the facing surfaces are spaced apart sufficiently to receive the two segments and the connection site between the facing surfaces and a second position in which the facing surfaces apply a force to the connection site substantially in alignment with the connection site axis, the roller being movable laterally back and forth relative to the plate when in the second position, the method comprising:
   a) forming the connection site with the connection forming apparatus;
   b) placing the connection site between the facing surfaces of the connection site opening station;
   c) moving the surfaces of the connection site opening station to compress the connection site substantially perpendicular to the connection site axis; and
   d) rotating the connection site substantially about the connection site axis.

12. The method of claim 11 in which the compressing and rotating occur simultaneously.

13. The method of claim 11 in which the connection site is rotated in a first direction and then in a second direction.

14. The method of claim 13 in which the connections site is rotated a first amount in the first direction and a second amount in the second direction.

15. The method of claim 14 in which the first amount and second amount are fixed.

16. The method of claim 14 in which the first amount and second amount are variable.

17. The method of claim 14 in which the first amount is different from the second amount.

18. The method of claim 14 in which the first amount is equal to the second amount.

19. The method of claim 14 in which the first amount is less than the second amount.

20. The method of claim 14 in which the first amount is greater than the second amount.

* * * * *